Figure 1:
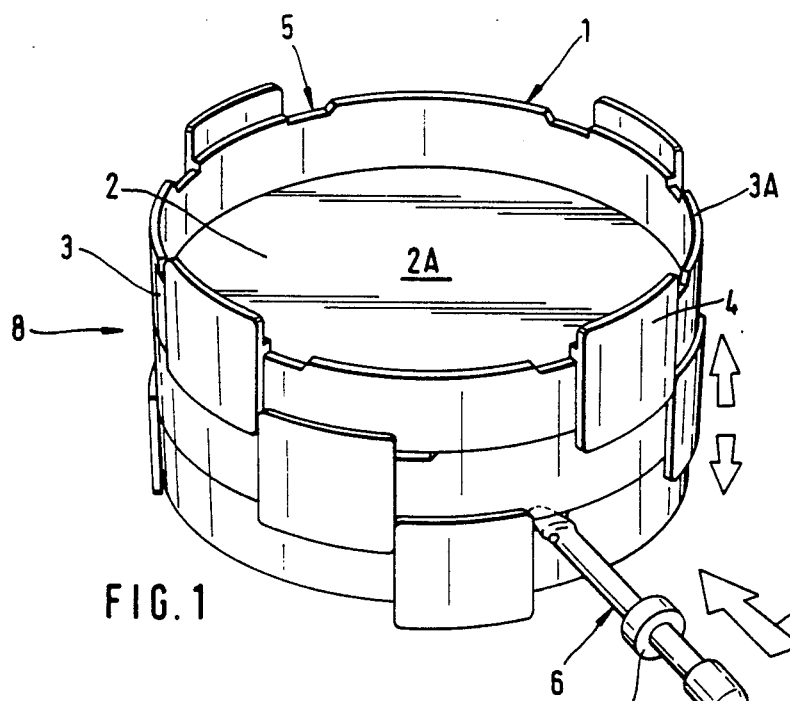

United States Patent [19]

Larsson et al.

[11] Patent Number: 4,488,583

[45] Date of Patent: Dec. 18, 1984

[54] ARRANGEMENT TO MAKE POSSIBLE THE SUPPLY OF MATERIAL TO RECEPTACLES AND MEANS THEREFORE

[75] Inventors: Peter L. Larsson, Mölndal; John-Erik B. Brorson, Västra Frölunda, both of Sweden

[73] Assignee: AB Centor SA, Goteborg, Sweden

[21] Appl. No.: 469,961

[22] Filed: Feb. 25, 1983

[30] Foreign Application Priority Data

Feb. 26, 1982 [SE] Sweden .................................. 8201205

[51] Int. Cl.³ ............................................... B65B 3/04
[52] U.S. Cl. .................................... 141/311 R; 141/392
[58] Field of Search ........................................ 141/1-12, 141/311 R, 392, 277

[56] References Cited

U.S. PATENT DOCUMENTS 3,120,249  2/1964  Keene .................................. 141/277

*Primary Examiner*—Houston S. Bell, Jr.
*Attorney, Agent, or Firm*—Balogh, Osann, Kramer, Dvorak, Genova & Traub

[57] ABSTRACT

The present invention relates to an arrangement and a device for making possible the supply of material to receptacles of the type intended to contain culture material. The receptacles are adapted to be arranged in a pile, one receptacle being placed on top of another receptacle. Each of the receptacles is provided with a bottom surface on which the material is deposited and a wall projecting upwardly from the bottom surface at right angles thereto. A plurality of piling projections extends along the wall of each of the receptacles in both upwards and downwards directions from the bottom surface, to a level above the upper peripheral edge of the wall, and to a level below that of the peripheral edge of the bottom surface, respectively, so as to make it possible for the receptacles to be arranged in a pile with the projections gripping the edges of upper and lower receptacles, respectively, and the receptacles receiving the intended culture material by means of a supply device.

8 Claims, 10 Drawing Figures

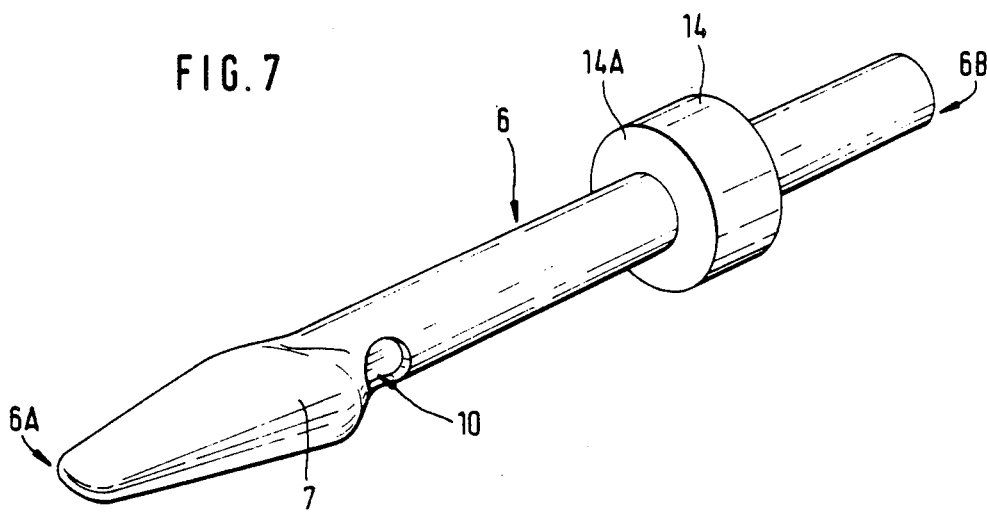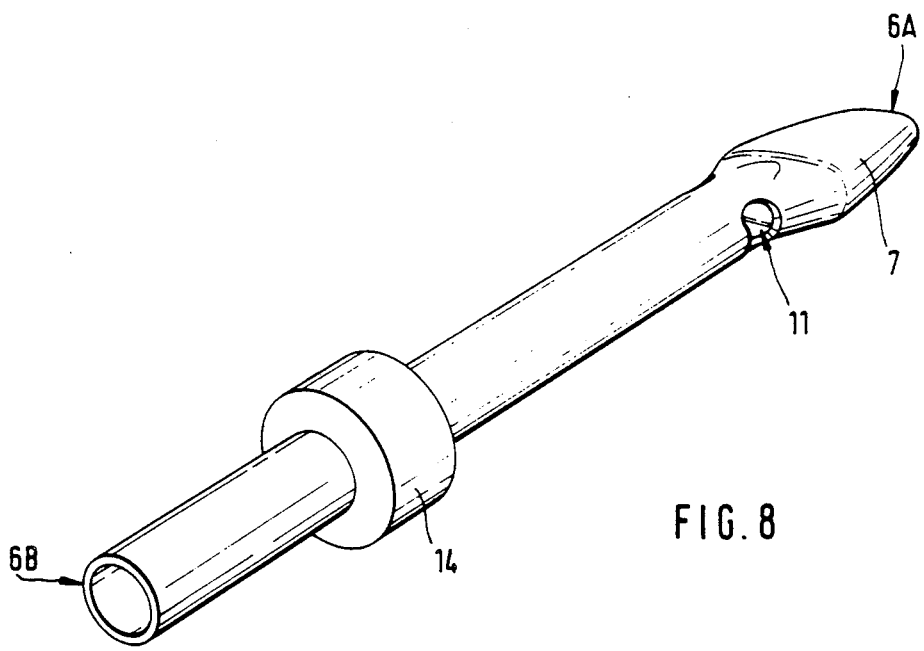

ARRANGEMENT TO MAKE POSSIBLE THE SUPPLY OF MATERIAL TO RECEPTACLES AND MEANS THEREFORE

The present invention relates to a method to make possible the supply of material to receptacles, which are adapted to form a pile, one receptacle being placed on top of another receptacle.

The invention also relates to a device for carrying out said method.

The type of receptacles to be considered in the first place are such receptacles as are used in connection with cultures, where some kind of an agar-agar compound is introduced into the receptacles, the latter ones being adapted to be piled up, one receptacle being placed on top of another receptacle. Such a receptacle is already known by way of example from the U.S. Pat. No. 3,198,713, but the known receptacles are not adapted to permit a rational supply of material to the same when they shall be piled one on top of the other, as at the moment of supply of for example agar-agar they must be handled one by one. Neither can any efficient ventilation of the space formed between two juxtapositioned receptacles of the known type take place, as they together define a substantially closed cavity.

It is a principal object of the present invention to provide a method of the kind mentioned above, which makes possible an efficient and rational supply of material to receptacles piled on top of each other.

The object is obtained by means of a method according to the present invention, which is substantially characterized by juxtapositioned receptacles, preferably by means of a feeder device arranged to supply the material, by tilting action being caused to separate in order to increase the space between them, whereafter the material is supplied to one of the two receptacles.

It is an additional object of the present invention to provide a means, which is well suited to be used when carrying out the method in question.

The additional object is obtained by means of a device according to the present invention, which is substantially characterized by a number of receptacles exhibiting a wall projecting from the bottom surface, on which material shall be deposited, being provided with a number of piling projections extending along said wall, which piling projections extend up to a level above the top portion of the wall and down to a level below the bottom of the receptacle, as seen, when the receptacle occupies a position, in which it is prepared to receive material.

Figure 2:
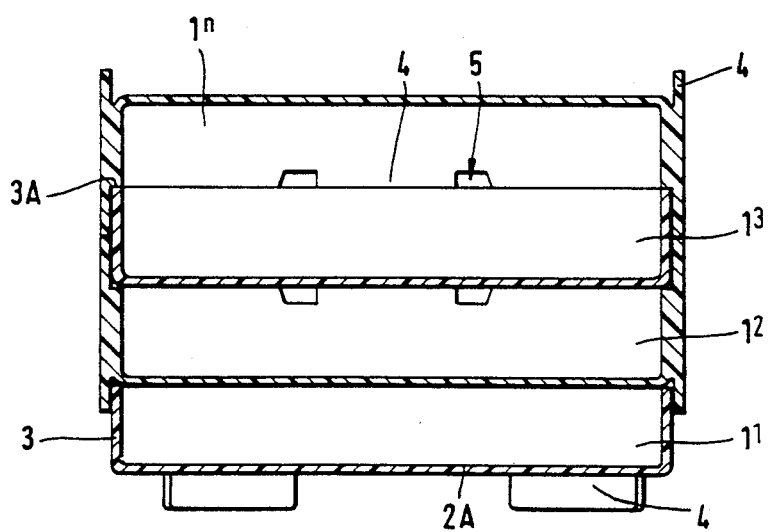
Figure 3:
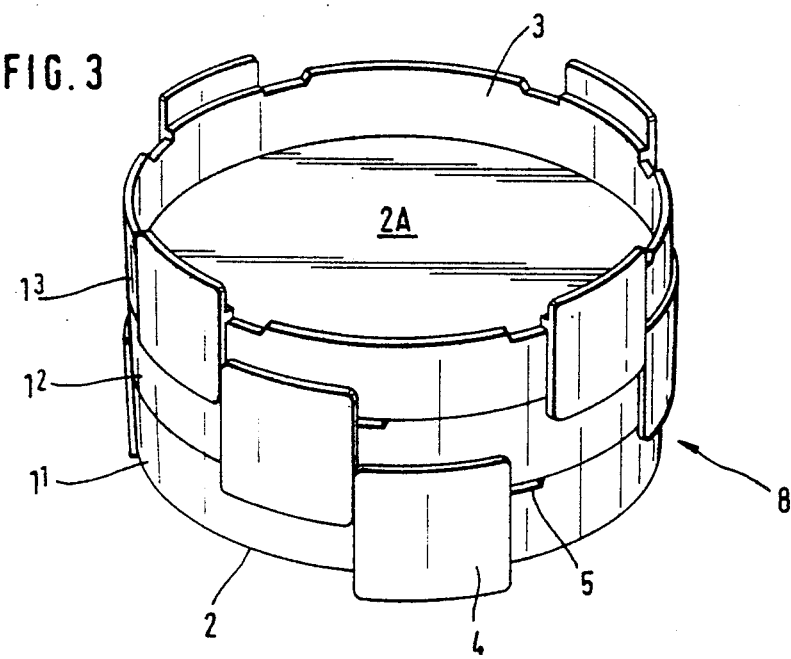
Figure 4:
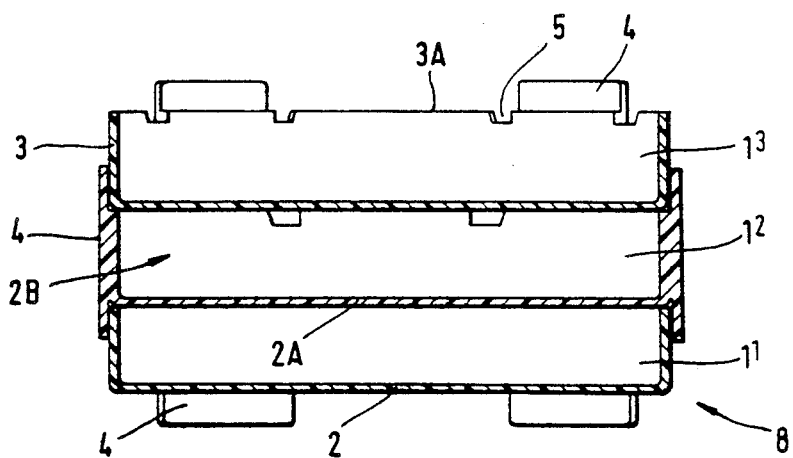
Figure 5:
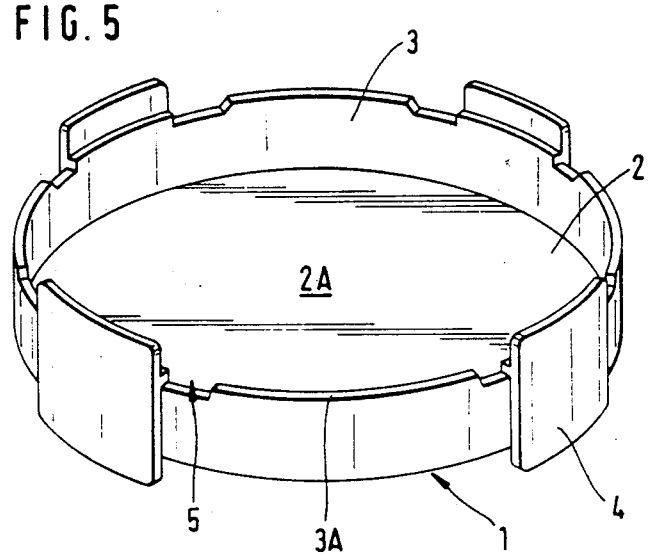
Figure 6:
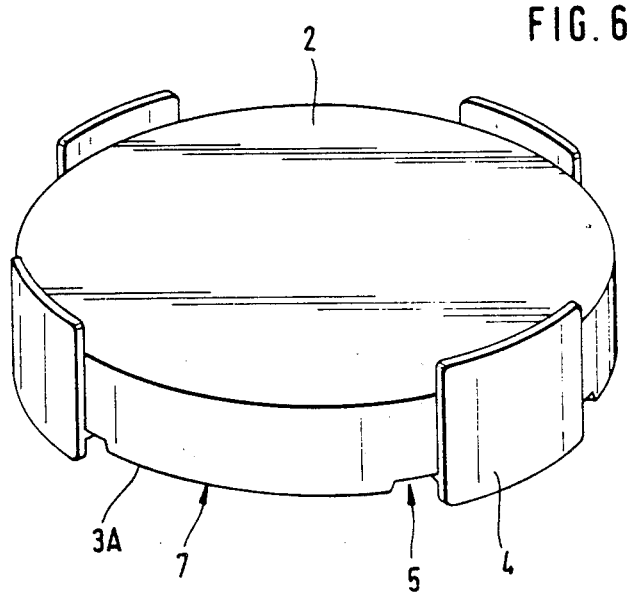
Figure 9:
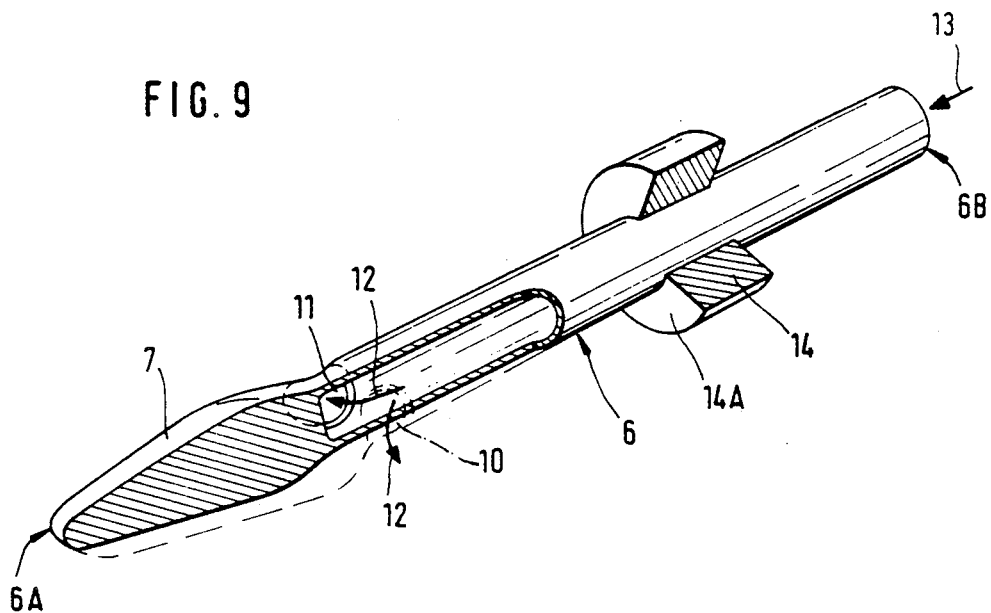
Figure 10:
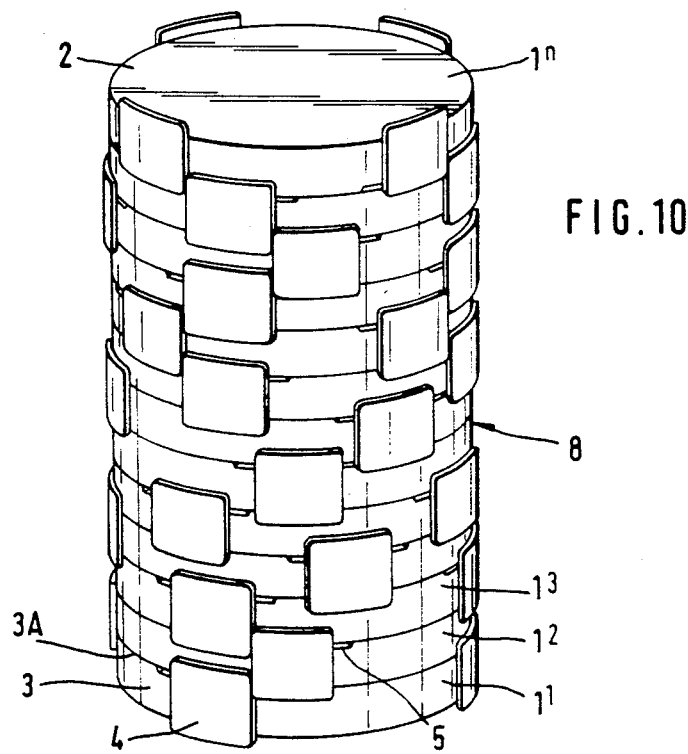

The invention is described in the following by means of an example of embodiment, reference being made to the accompanying drawings, in which:

FIG. 1 illustrates the invention adapted to a number of receptacles placed one on top of another and forming a pile, a feeder device intended for the supply of material to the receptacles being inserted between two receptacles, FIG. 2 is a view of a pile of receptacles as seen in longitudinal cross-section, the uppermost located receptacle of the pile being turned upside down in order to form a receptacle lid, FIG. 3 is a perspective view of a pile of receptacles in upright position, FIG. 4 is a view of a longitudinal cross-section of the pile of receptacles illustrated in FIG. 3, FIG. 5 is a perspective view of a receptacle in upright position, FIG. 6 is a perspective view of a receptacle in upside down position, FIG. 7 is a perspective front view of a feeder device intended for the supply of material to the receptacles, FIG. 8 is a view of the feeder device illustrated in FIG. 7 as seen in an oblique direction from its rear portion, FIG. 9 is a partially sectional view of the feeder device, and FIG. 10 is a perspective side elevational view of a pile, which is formed by a number of juxtapositioned receptacles.

A receptacle made according to the present invention and in the drawings indicated with the digit 1 is in the illustrated example of embodiment formed by a bottom portion 2 of cylindrical shape and preferably made of plastic material, to which bottom portion a lateral wall 3 is connected. The lateral wall 3 suitably forms an integrated part with the preferably flat bottom portion 2 and suitably extending at a right angle to the same. A suitable number of preferably plate shaped and curved elements 4 are interspaced along the periphery of the receptacle at suitable mutually distances from each other. The elements 4 are radially displaced relative to the lateral wall 3 and extend in axial direction along the wall 3 to an upper level, that is higher than the free upper peripheral edge 3A of the wall, and to a lower level, that is below the level of the bottom portion 2. The elements 4, which are intended to make possible the piling up of the receptacles 1 on top of each other, preferably constitute an integrated part of the wall 3 of the receptacle, and the whole receptacle 1 is suitably manufactured of plastic material by an injection moulding process.

In the area preferably close to each one of the projecting piling elements 4 there are holes 5 of preferably slit shaped form made in the wall 3, the width of said holes permitting the introduction of the front end 6A of the front portion 7 of a device 6 intended for the supply of material such as by way of example agar-agar to a surface 2A of the bottom 2 of the receptacle, on which it shall be deposited. The openings 5 also serve the purpose to provide an efficient ventilation between the inner cavity 2B of the receptacle and the surrounding air, when a number of receptacles 1 are piled on top of each other forming a pile, as is shown in FIGS. 1-4 of the drawings. For this purpose the openings 5 are interspaced along the periphery of the receptacle in such a manner that at least one opening 5 always is located at a certain distance from the projecting piling element 4, when a number of receptacles 1 are arranged to form a pile 8, as is evident from the drawings.

The supply device 6 is in the illustrated embodiment a nozzle-like tubular injecting device 6, which can be manually operated and be connected with a container holding the material. The connection to a storage container, not shown in the drawings, which is designed to hold for example agar-agar, can be in the form of a hose 9 or any other suitable connecting means. The supply device 6 exhibits a front portion 7 of preferably conical section tapering towards its nib-like and somewhat flattened closed end 6A. In the area behind said front portion 7, as seen in direction away from the front end 6A of the supply device, there are two output openings 10 and 11 respectively facing away from each other in opposite directions and intended for the output of material introduced at the rear end 6B, the input and output directions of the material being indicated by the arrows 13 and 12 respectively. A stop dog 14 in the form of a collar is connected with the supply device 6 at a suitable distance from the two ends 6A, 6B of the same, and, if placed in a correct manner with the centre of gravity of the device 6 at a suitable point, it makes possible that the mouth piece device 6 can be placed on a support, such as for example a table, and be supported by said stop dog 14, the device 6 substantially occupying a horizontal position with the output openings 10, 11 located on a level above the table, so that impurities etc. are impeded to reach the portion 6A of the device 6, which is intended to be introduced through said openings 5 of the receptacles 1. The stop dog 14 also serves as a stop with its lateral surface 14A facing the front portion 6A of the device 6 in order to prevent the same from being inserted too far inwards into the cavity 2B of the receptacle 1 through said opening 5.

As is clearly evident from FIG. 1, juxtapositioned receptacles 1¹, 1², 1³ etc., which are placed on top of each other in order to form a pile 8, by tilting action will be caused to be separated from each other in an oblique manner in the directions indicated with arrows in FIG. 1, when the supply device 6 is inserted through an opening 5 of one receptacle 1¹, whereby the interspace between the two receptacles 1¹, 1² located above and beneath said supply device 6 increases. The supply device 6 is inserted through the opening 5 to such an extend that the lateral surface 14A of the stop dog 14 will abut against the wall 3 of the receptacle 1 and thereby impede any further introduction of the same, whereafter the agar-agar or any other suitable compound will be supplied to the surface 2A of deposit of a receptacle 1¹ via the output openings 10, 11 of the supply device 6. The operation can thereafter be continued until all receptacles will have received a deposit of agar-agar etc. on their respective surfaces 2A of deposit.

As is shown in FIGS. 2 and 10, the receptacle 1ⁿ located uppermost in the pile 8 can suitably be turned upside down, so that its bottom 2 will form a lid. The operating interspace between the two receptacles 1 exhibiting surfaces of deposit 2A facing each other is also increased, which arrangement also can be desirable in certain other cases, and therefore also can be applied to receptacles 1 by way of example located in the middle of a pile 8. The piling elements 4 extend along the outside of the walls 3 of those receptacles 1, which are located close on top of and/or below said receptacles 1, while the piling elements 4 of said receptacle in its turn abut along the outside of said receptacle 1. An effective guide of the receptacles 1 is thereby obtained, and the receptacles are moreover impeded from drawing away from each other in sideways direction.

The receptacles 1 are suitably delivered to the user in a pile 8, and he will then only have to perform the simple task of supplying material to them.

The invention is not limited to the embodiment described above and illustrated in the drawings by way of example only, but can be varied as to its details within the scope of the following claims. The receptacles can by way of example be designed with a shape deviating from the circular shape, for example being square, and the piling elements are then suitably arranged at the corners of the respective receptacle.

We claim:

1. In an arrangement for making possible the supply of material to receptacles of the type intended to contain culture material, which receptacles are adapted to be arranged in a pile, one receptacle being placed on top of another receptacle, the improvement comprising a plurality of receptacles, each of which is provided with a bottom surface on which material is deposited, and a wall projecting upwardly from the bottom surface, and a plurality of piling projections extending along the wall of each of said plurality of receptacles in upwards and downwards directions from the bottom surface to a level above the free upper peripheral edge of the wall and to a level below that of the peripheral edge of the bottom surface, respectively, so as to make it possible for said plurality of receptacles to be arranged in a pile, which said projections gripping the edges of upper and lower receptacles of said plurality of piled receptacles, respectively, and said receptacles receiving intended culture material.

2. The improved arrangement according to claim 1, wherein the wall extends at right angles to the bottom surface, and the projections being radially displaced relative to the wall, so to make possible the use of a receptacle placed on top of another one as a cover.

3. The improved arrangement according to claim 1 or 2, wherein the piling projections comprise plate-like curved elements which are connected to the wall of each of said receptacles, and extend in axial direction therealong, said elements being arranged to abut against the outside of the wall of a juxtapositioned receptacle in the pile.

4. The improved arrangement according to claim 1, further comprising a plurality of openings being provided in the interspace between two juxtapositioned receptacles, for making possible passing into and out of the space between said receptacles.

5. The improved arrangement according to claim 4, wherein the openings comprise recesses formed in the wall of each of said receptacles.

6. The improved arrangement according to claim 5, wherein the recesses are located in the wall in areas close to a piling projection.

7. The improved arrangement according to claim 5, wherein the openings are located close to the free peripheral edge of the wall, and comprise a slit extending along the wall.

8. The improved arrangement according to claim 1, further comprising a supply device for separating said receptacles one from each other, said device comprising nozzle-like injection means having a conical inserting portion tapering in direction towards the front edge thereof.

* * * * *